(12) United States Patent
Haecker et al.

(10) Patent No.: US 8,202,489 B2
(45) Date of Patent: Jun. 19, 2012

(54) DISPOSABLE CASSETTE

(75) Inventors: Juergen Haecker, Neu-Anspach (DE); Stephan Frey, Frankfurt (DE); Uwe Lapp, Butzbach (DE); Paul Jahn, Frankfurt (DE); Stephan Oesterreich, Neu-Anspach (DE)

(73) Assignee: Fresenius Medical Care Deutschland GmbH, Bad Homburg v.d.H. (DE)

( * ) Notice: Subject to any disclaimer, the term of this patent is extended or adjusted under 35 U.S.C. 154(b) by 0 days.

(21) Appl. No.: 12/805,124

(22) Filed: Jul. 13, 2010

(65) Prior Publication Data
US 2011/0070132 A1    Mar. 24, 2011

Related U.S. Application Data

(63) Continuation of application No. 10/525,668, filed as application No. PCT/EP03/09128 on Aug. 18, 2003, now abandoned.

(30) Foreign Application Priority Data

Aug. 28, 2002 (DE) .................................. 102 39 597

(51) Int. Cl.
*B01L 3/00* (2006.01)

(52) U.S. Cl. ............................ 422/501; 422/500; 422/50

(58) Field of Classification Search .................. 422/102, 422/103, 50, 500
See application file for complete search history.

(56) References Cited

U.S. PATENT DOCUMENTS

| | | | |
|---|---|---|---|
| 4,585,623 A | 4/1986 | Chandler | |
| 4,978,502 A | 12/1990 | Dole et al. | |
| 5,580,523 A | 12/1996 | Bard | |
| 5,660,728 A * | 8/1997 | Saaski et al. | 210/251 |
| 6,261,066 B1 | 7/2001 | Linnemann et al. | 417/53 |
| 7,238,325 B2 * | 7/2007 | Anazawa et al. | 422/103 |
| 2002/0081222 A1 * | 6/2002 | Karp | 417/507 |
| 2003/0051339 A1 * | 3/2003 | Ehrfeld et al. | 29/830 |

FOREIGN PATENT DOCUMENTS

| | | |
|---|---|---|
| DE | 38 00 036 A1 | 7/1988 |
| EP | 1 327 474 A1 | 7/2003 |
| JP | 2000 508058 | 6/2000 |
| JP | 2002 219697 | 8/2002 |
| WO | WO 97/22825 | 6/1997 |
| WO | WO 01/72467 | * 10/2001 |
| WO | WO 02/24320 A1 | 3/2002 |

OTHER PUBLICATIONS

Jaroschek C., et al., "Combining Hard and Soft Plastics in Injection Moulding," Kunststoffe, Carl Hanser Verlag., pp. 705, 706, 708, 710, Jun. 1994. (Abstract only).

(Continued)

*Primary Examiner* — Christine T Mui
(74) *Attorney, Agent, or Firm* — Jacobson Holman PLLC

(57) ABSTRACT

A disposable cassette, preferably for use in analysis technology, has at least one first part in which channel structures are cut out in the surface and a second part covering the first part in a sealing manner, with engagement regions for actuator elements being provided at pre-determined points. The first part and/or the second part are constructed of a rigid material and have a flexible material region associated therewith, with the rigid material and the flexible material region being manufactured in one piece using two-component injection molding technology.

11 Claims, 2 Drawing Sheets

OTHER PUBLICATIONS

Steinbichler, G., et al., "In Combination with Liquid Silicone Rubbers," Kunststoffberater, Kunststoff Verlag, pp. 28-30, May 1999. (Abstract only).

Freyer C., et al., "In Combination with Silicone Elastomers", Kunststoffberater, Kunststoff Verlag., pp. 27-30, Jul. 2000. (Abstract only).

Hunold D., et al., "A Clever Combination—An Economical Production," Kunststoffe, Carl Hanser Verlag., pp. 108-110, Mar. 2001. (Abstract only).

English Translation of rejection of Patent Application. No. JP. 2004-535103, May 12, 2009, pp. 1-18.

* cited by examiner

DISPOSABLE CASSETTE

CROSS-REFERENCE TO RELATED APPLICATION

This application is a continuation application of U.S. application No. 10/525,668, filed Feb. 25, 2005 now abandoned, the disclosure of which is incorporated by reference as if fully set forth herein.

U.S. application No. 10/525,668 is a nationalization of PCT/EP03/009128 filed Aug. 18, 2003, and published in German.

BACKGROUND OF THE INVENTION

1. Field of Invention

The invention relates to a disposable cassette having at least one first part in which channel structures are cut out in the surface and a second part covering the first part in a sealing manner, with engagement regions for actuator elements being provided at pre-determined points.

2. Description of the Prior Art

Disposable plastic articles with fluid carrying channels are frequently used in medical equipment. Corresponding cassette systems have proven their worth here as alternatives to conventional hose systems. The corresponding fluid paths are formed in these cassette systems. The fluid flowing through the fluid paths is acted on by means of corresponding actuators. For instance, valves are used via which the fluid paths are switched open or are closed. On the other hand, pumps for the transport of the fluid are integrated in such cassette systems. In the field of medical application, disposable cassettes are already known in which a rigid part is provided into which channels and chambers are formed. This rigid part is covered by a continuously flexible film.

In the field of analysis technology, the known cassette systems frequently have a very complex design. On the one hand, they have rigid boundaries and, on the other hand, they have regions for the installation of actuator elements. The systems used in analysis technology are usually made in three layers in that, in addition to two rigid layers, a flexible film is also provided through which the fluid flow can be manipulated at exposed regions.

A genetic disposable cassette for use in analysis technology is already known from WO 02/24320A1 which consists of a first part in which channel structures are cut out in the surface. This first part is sealingly covered via a second part. One of the two parts is made as a flexible part. Engagement regions for actuator elements are provided at pre-determined points of this disposable cassette. The forming of one of the two parts of the already known disposable cassette as a flexible part is, however, disadvantageous since the stability and also the functionality of the individual sealing function of the total disposable cassette is not always ensured.

SUMMARY OF THE INVENTION

It is therefore the object of the present invention to further develop a generic disposable cassette such that it has a simple design, on the one hand, and has a design stable per se, on the other hand.

This object is solved in accordance with the invention by a disposable cassette having the features described herein. Accordingly, the first part and/or the second part are, for the larger part, rigid in design. However, respective flexibly designed regions can be provided, with the rigid and flexible regions each being manufactured in one piece using two-component injection molding technology. The rigid part can thereby be manufactured as one component with the integrated flexible regions and can thus be manufactured in a cost-favorable manner in a single production step. On the other hand, a high stability of the total component results here in comparison with the prior art. A more compact design also results due to the fewer layers required with respect to other disposable cassettes of a more complex design in analysis technology.

Advantageous aspects of the invention are recited in the dependent claims.

Accordingly, the flexible regions can be formed in the engagement regions for the actuator elements.

On the other hand, at least some of the channels can consist of flexible material.

Valves, membrane pumps, restrictors or metering valves can be used as actuators.

The region of the channels in which the actuators are coupled is advantageously made shallower and with a larger channel cross-section. The required actuator forces for the deflection of the flexible region can be reduced by these aspects.

Both liquids and gases can be the fluid for the flowing through of the channels.

The cassette in accordance with the invention is preferably used in medical engineering in the conveying and/or metering of fluids. It is particularly suitable for conveying and/or metering in analysis technology.

BRIEF DESCRIPTION OF THE DRAWINGS

Further details and advantages of the invention will be explained in more detail with reference to embodiments shown in the drawing. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 2:
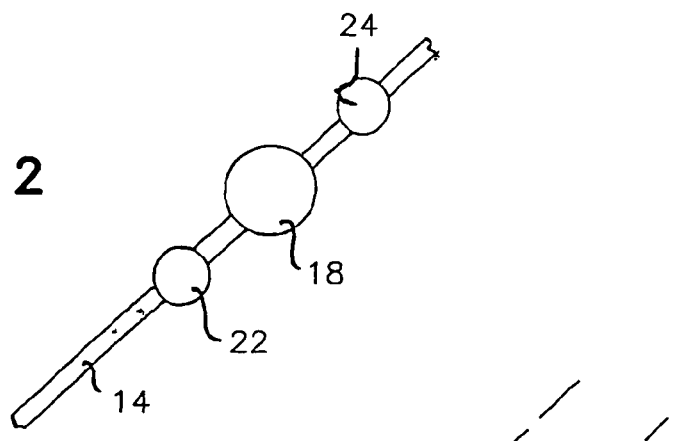
FIG. 2: a schematic representation of the arrangement of different, actuators along a channel in a disposable cassette in accordance with FIG. 1.
Figure 1:
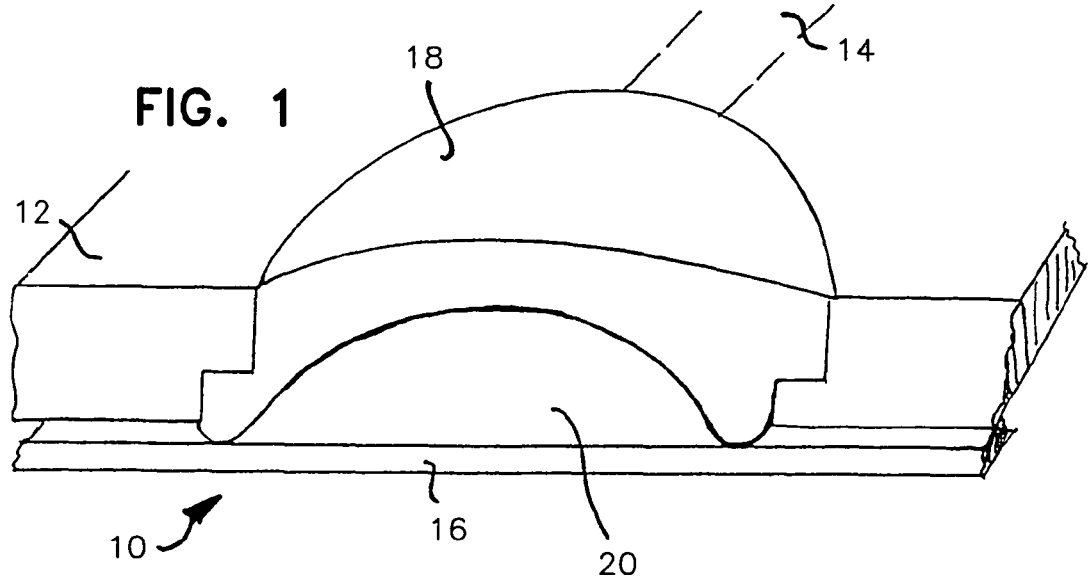
FIG. 1: a schematic, perspective detailed view of a partly sectioned disposable cassette in accordance with a variant of the present invention.

In the disposable cassette 10 shown partly in FIG. 1, a channel structure 14 is formed for the purpose of fluid guidance in a first part 12 and is tightly closed by a second part 16, a type of rigid cover plate. A partial region 18 of the first part 12, which otherwise consists of a rigid plastic material, is made as an integral component of the part 12 in a flexible elastomer material. This elastomer region 18, which is made in one piece, serves as a pump calotte. The pump calotte is moved to and fro by being acted on by means of a corresponding actuator, which is not shown in more detail here in FIG. 1, such that the space 20 sealingly surrounded by the pump calotte 18 is reduced or enlarged in volume. This space 20, which is in communication with the channel 14, is filled with the fluid to be conveyed so that the fluid can be conveyed accordingly by a corresponding deflection of the elastomer component 18, i.e. the pump calotte. This conveying principle corresponds precisely to that of a membrane pump and is already known as a principle both in analysis technology and overall in medical engineering. It is indicated in FIG. 2 that valves 22 and 24 are provided at the inlet and outlet sides respectively in the channel 14 next to the flexible region 18 which serves as a pump calotte, said valves being attached as backflow valves which are closed and opened alternately in tact with the pump. These regions can also be made as correspondingly flexible partial regions of the otherwise rigid first part 12 of the disposable cassette 10. The first part 12 can be produced as a one-piece element using two-component injection molding technology.

Figure 3:
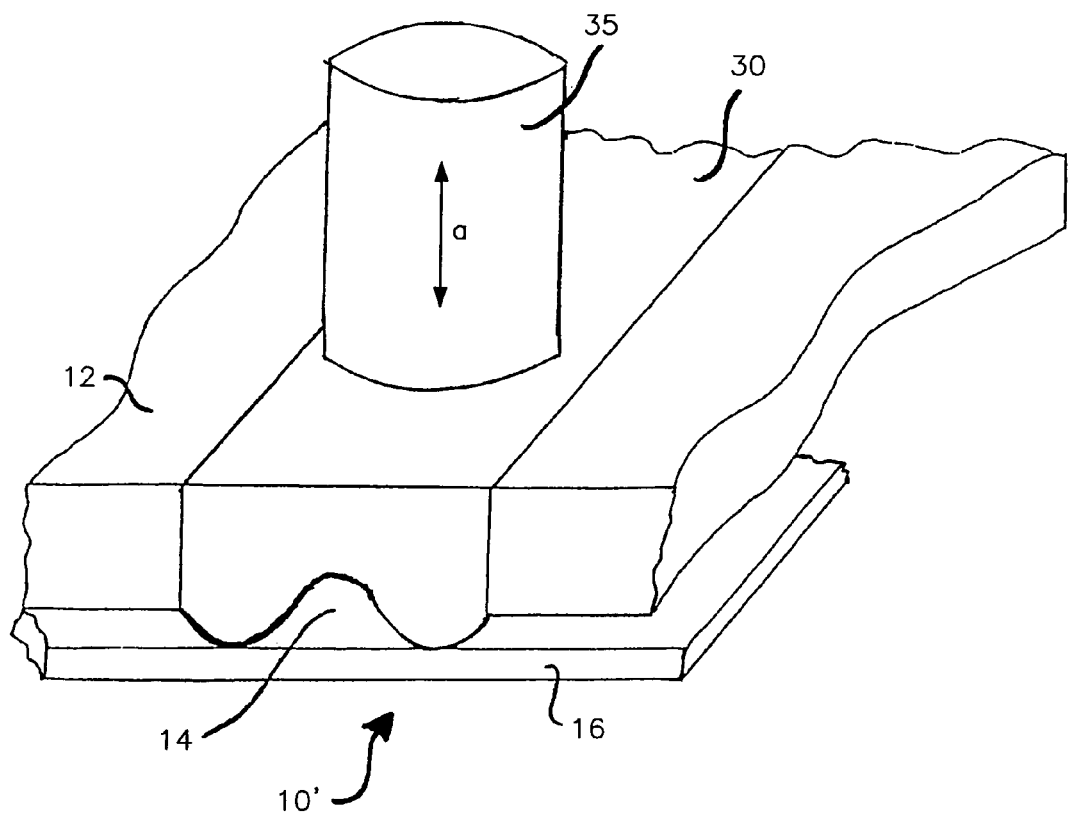
FIG. 3: a perspective representation of a further embodiment of the disposable cassette in accordance with the invention as a cut-out detail.

Another embodiment variant of a disposable cassette 10' is realized in FIG. 3. A channel structure 14 which is downwardly tightly closed by the second part 16, which is made as a rigid cover plate, is formed in a first part 12 of the disposable cassette 10' for the purpose of fluid guidance. The channel 14 can be opened and closed in the flow direction by a channel section 30 which is made in a flexible elastomer material and which was manufactured in one piece with the first part 12 by two-component injection molding technology. The resilient region 30 is an integral component of the otherwise rigid first part 12 due to this one-piece formation. It is thereby connected to it firmly, on the one hand, and in a liquid-tight manner, on the other hand.

It is sufficient for the closing of such a valve to guide the force of a plunger 35 to the rear side of the resilient region 30 in the direction a of the double arrow. The channel 14 is closed due to this force discharge. The opening of the valve takes place by removing the closing force, i.e. by the withdrawing of the plunger 35 in the direction a of the double arrow such that the region 30 is again shaped back into the original channel form by its resilient material properties In the embodiment shown here, the channel 14 is made continuously as a flexible elastomer part. Alternatively to this, however, the channel can be made as a flexible elastomer part only in the region of the valve itself, while the other channel regions are formed by means of the rigid material of the first part 12. The force discharge onto the flexible elastomer region can take place in a variety of ways. On the one hand, in a tactile manner via a plunger 35, as shown in FIG. 3. On the other hand, however, also directly pneumatically via compressed air. In this case, a sealing lip would have to be provided around the valve on the rear side of the first part 12. Finally, the force can also be applied indirectly pneumatically or hydraulically via a small pressure cushion which would have to be provided on the instrument side. It is particularly advantageous here for a sealing function already being able to be achieved with very small valve closing forces.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A disposable cassette comprising
   at least one first part in which channel structures are provided in a surface thereof, and a second part covering the first part in a sealing manner, with engagement regions for actuators being provided in the first part at predetermined points,
   the first part having a construction that includes a rigid material with a flexible material region associated therewith, with the rigid material and the flexible material region being of a one piece, two-component injection molded construction,
   both the channel structures and the engagement regions for the actuators being provided in the flexible material region.
2. The disposable cassette in accordance with claim 1, wherein the actuators are valves.
3. The disposable cassette in accordance with claim 1, wherein the actuators are membrane pumps.
4. The disposable cassette in accordance with claim 1, wherein the actuators are at least one of restrictors and metering valves.
5. The disposable cassette in accordance with claim 1, wherein the engagement region of the channel is shallower and has a larger channel cross-section relative to a remaining region of the channel.
6. The disposable cassette in accordance with claim 2, wherein the engagement region of the channel is shallower and has a larger channel cross-section relative to a remaining region of the channel.
7. The disposable cassette in accordance with claim 3, wherein the engagement region of the channel is shallower and has a larger channel cross-section relative to a remaining region of the channel.
8. The disposable cassette in accordance with claim 4, wherein the engagement region of the channel is shallower and has a larger channel cross-section relative to a remaining region of the channel.
9. A disposable fluid cassette comprising:
   (i) a first part that includes a rigid plastic portion and a flexible elastomeric material portion, the flexible elastomeric material portion being integral with the rigid plastic portion by a one piece, two-component injection molded construction,
   the flexible elastomeric material portion including a channel for guiding a fluid and an engagement region for cooperation with a fluid transport actuator, and
   (ii) a second part having a rigid construction that sealingly covers the first part, the engagement region being configured to be acted upon by the actuator such that a space defined by the flexible elastomeric material, which is in communication with the fluid guidance channel, is reduced or enlarged in volume so as to convey the fluid therethrough.
10. The disposable fluid cassette according to claim 9, wherein the engagement region of the channel is shallower and has a larger channel cross-section relative to a remaining region of the channel.
11. The disposable fluid cassette according to claim 9, wherein portions of the flexible elastomeric material portion of the first part that are located at edges of the channel contact the second part to provide a sealed engagement.

* * * * *